United States Patent
Qu

(10) Patent No.: US 8,114,039 B2
(45) Date of Patent: Feb. 14, 2012

(54) SYSTEM AND METHOD FOR SWEAT AND TEMPERATURE CONTROL IN THE TREATMENT OF POSITIONAL PLAGIOCEPHALY

(75) Inventor: Wei Qu, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 720 days.

(21) Appl. No.: 12/202,463

(22) Filed: Sep. 2, 2008

(65) Prior Publication Data

US 2009/0118654 A1   May 7, 2009

Related U.S. Application Data

(60) Provisional application No. 60/984,502, filed on Nov. 1, 2007.

(51) Int. Cl.
 *A61F 5/00* (2006.01)
 *A42B 1/00* (2006.01)
(52) U.S. Cl. ............... 602/17; 602/14; 128/857; 2/410
(58) Field of Classification Search ............. 602/14, 602/17; 128/857; 2/4–15, 410–454
 See application file for complete search history.

(56) References Cited

U.S. PATENT DOCUMENTS

| | | | |
|---|---|---|---|
| 4,466,138 A * | 8/1984 | Gessalin | ............................ 2/410 |
| 4,776,324 A | 10/1988 | Clarren | |
| 5,951,503 A | 9/1999 | Pomatto | |
| 6,423,019 B1 | 7/2002 | Papay et al. | |
| 6,592,536 B1 | 7/2003 | Argenta | |
| 7,127,101 B2 | 10/2006 | Littlefield et al. | |
| 7,142,701 B2 | 11/2006 | Littlefield et al. | |
| 7,162,075 B2 | 1/2007 | Littlefield et al. | |
| 7,177,461 B2 | 2/2007 | Littlefield et al. | |
| 7,242,798 B2 | 7/2007 | Littlefield et al. | |
| 7,305,369 B2 | 12/2007 | Littlefield et al. | |
| 7,566,313 B1 * | 7/2009 | Argenta | ............................ 602/17 |
| 2005/0050617 A1 * | 3/2005 | Moore et al. | ..................... 2/410 |

OTHER PUBLICATIONS

Ripley et al., "Treatment of Positional Plagiocephaly Uitlizing the Cranial Remodeling Orthosis [Dynamic Orthotic Cranioplasty (DOC)]", Proceedings of the 5th International Congress of the International Society of Craniofacial Surgery, pp. 111-114, 1994.
Cranial Technologies, PhotoStudy, Cranial Helmet used 03/04 until 12/04, Mar. 11, 2005, 2 pages, Glenview, IL.
Cranial Technologies, photographs dated Dec. 9, 2002, 2 pages.
Cranial Technologies, PhotoStudy, photographs, dated Apr. 19, 2006, 2 pages, Glenview, IL.

* cited by examiner

*Primary Examiner* — Patricia Bianco
*Assistant Examiner* — Keri J Nelson
(74) *Attorney, Agent, or Firm* — Alexander J Burke

(57) ABSTRACT

A system and method are disclosed for providing a ventilated orthotic cranioplasty helmet for treating positional plagiocephaly in infants. Specifically, a system and method are disclosed in which patient-specific parameters such as head size, patient age, degree of patient sweating, diameter of patient's hair, average length of patient's hair, and sweat range are input into a computer implemented algorithm along with a user-proposed ventilation hole array to determine an optimal ventilation hole arrangement. The computer may be connected either directly or indirectly to an automated hole drilling machine to drill the hole array in the specified portion of the helmet. The same computer implemented algorithm can be used to revise the ventilation hole array to accommodate changes in patient physiology during treatment to thereby achieve an optimal ventilation hole design throughout the treatment process.

20 Claims, 7 Drawing Sheets

SYSTEM AND METHOD FOR SWEAT AND TEMPERATURE CONTROL IN THE TREATMENT OF POSITIONAL PLAGIOCEPHALY

This is a U.S. non-provisional application of U.S. provisional patent application Ser. No. 60/984,502, filed Nov. 1, 2007, by Wei Qu, the entirety of which application is incorporated herein by reference.

FIELD OF THE DISCLOSURE

The disclosure relates to systems and methods for treating positional plagiocephaly, and more particularly to an improved system and method for a ventilated orthotic cranioplasty helmet for treating positional plagiocephaly in infants.

BACKGROUND

Many infants have abnormal head shape, referred to as positional plagiocephaly, which may be caused by a variety of factors, such as birth trauma, premature birth, sleeping position, torticollis, cervical anomalies, lack of full bone mineralization, and the like. Such non-synostotic positional deformations must be treated to avoid potential undesirable effects to facial expressions and skull or cranial vault growth. Ripley et al, in "Treatment of Positional Plagiocephaly Utilizing the Cranial Remodeling Orthosis [Dynamic Orthotic Cranioplasty (DOC)]," *Proceedings of the 5th International Congress of the International Society of Craniofacial Surgery*, pp: 111-114 (1994), proposed a dynamic orthotic cranioplasty to treat the positional plagiocephaly. With the Ripley device, the head shape of the subject infant patient is first modeled. A helmet is then manufactured based on the head model, the helmet being configured to remodel the infant's head to the desired shape. During the treatment time, the helmet is periodically trimmed by trained specialists according to the progressive changes in the head's shape. FIGS. 1a-c illustrate the effect on an exemplary infant patient before and after the treatment. An example of a company that provides such helmets is Cranial Technologies, of Tempe, Ariz. In FIG. 1a, the infant patient's head can be seen to have the asymmetric geometry that is symptomatic of positional plagiocephaly. FIG. 1b shows the patient with a typical helmet designed to reshape the infant's head. FIG. 1c shows the same patient subsequent to treatment, in which it can be seen that the head now conforms to a desired generally symmetric shape.

Although effective and useful in the treatment of positional plagiocephaly, such helmets suffer from the problem that they trap heat at the patient's scalp, which can cause the patient to sweat due to the lack of adequate air venting. This can be a particular problem at or near the back of the head. The problem with such sweating is that it can hinder treatment effectiveness, since sweat can make the helmet slippery and thus may decrease the positioning accuracy. Moreover, excessive sweating may also enhance the growth of germs which can make the infant uncomfortable, make the skin irritable, and can result in a generally unhealthy condition. Wearing fewer clothes or using a fan facing the head may work as temporary solutions, but they too can be problematic because they may make the infant prone to catching cold. The use of cooling materials (e.g., ice) is not currently allowed without FDA approval because it may be unsafe. Cooling materials may also be too heavy for the infant's head.

Thus, there is a need for an enhanced design for a ventilated helmet for use in treating positional plagiocephaly. There is also a need for providing a system and method for designing an optimal helmet ventilation configuration based on specific parameters of the individual patient. Additionally, there is a need for a system and method for revising the helmet ventilation design during the treatment period to maintain optimum ventilation for the patient.

SUMMARY OF THE DISCLOSURE

In this present disclosure, a low cost solution is provided to address the problem of undesirable heat generation in helmets used for dynamic orthotic cranioplasty. The solution is safe, and it does not require the use of additional materials, yet it is effective at decreasing the likelihood of excessive sweating by allowing more air to access the occluded head area. Moreover, the design can be adaptive to different infants' heads as well as to the changes in an individual infant's head shape over time. Finally, the improvement will not negatively influence the patient's treatment (i.e., it will not compromise the operational efficiency of the orthosis).

A method for providing a customized orthopedic helmet, comprising: providing an orthopedic helmet with an array of ventilation holes; wherein at least one of: (a) the array of ventilation holes, and (b) a size of at least one of the ventilation holes, is configured based on a parameter selected from the list consisting of: helmet thickness, helmet diameter, patient age, degree of patient sweating, diameter of patient's hair, average length of patient's hair, and sweat range.

A system for providing a customized orthopedic helmet, comprising: means for providing an orthopedic helmet with an array of ventilation holes; wherein at least one of: (a) the array of ventilation holes, and (b) a size of at least one of the ventilation holes, is configured based on a parameter selected from the list consisting of: helmet thickness, helmet diameter, patient age, degree of patient sweating, diameter of patient's hair, average length of patient's hair, and sweat range.

A machine readable storage device tangibly embodying a series of instructions executable by the machine to perform a series of steps, the steps comprising: providing an orthopedic helmet with an array of ventilation holes; wherein at least one of: (a) the array of ventilation holes, and (b) a size of at least one of the ventilation holes, is configured based on a parameter selected from the list consisting of: helmet thickness, helmet diameter, patient age, degree of patient sweating, diameter of patient's hair, average length of patient's hair, and sweat range.

BRIEF DESCRIPTION OF THE DRAWINGS

The accompanying drawings illustrate preferred embodiments of the disclosure so far devised for the practical application of the principles thereof, and in which.

DETAILED DESCRIPTION

Figure 1C:
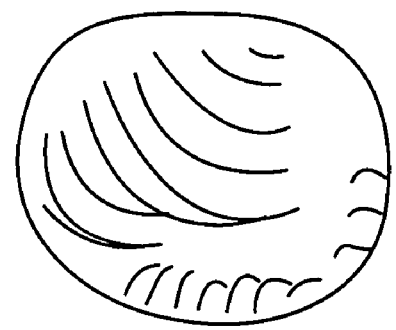
FIGS. 1a-1c show, respectively, an exemplary infant's head prior to treatment, an infant wearing a typical dynamic orthotic cranioplasty helmet, and the exemplary infant's heat subsequent to treatment.
Figure 1B:
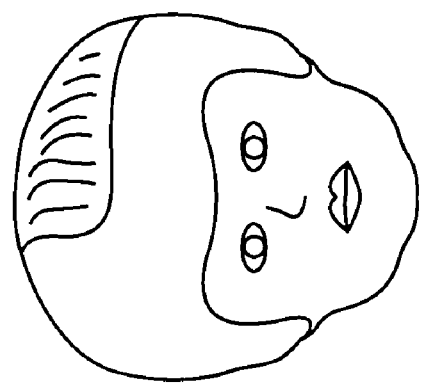
Figure 1A:
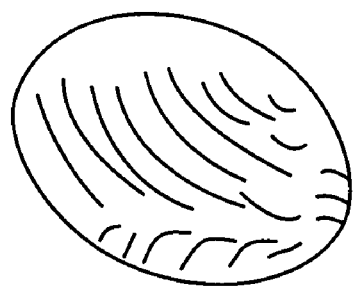
Figure 2:
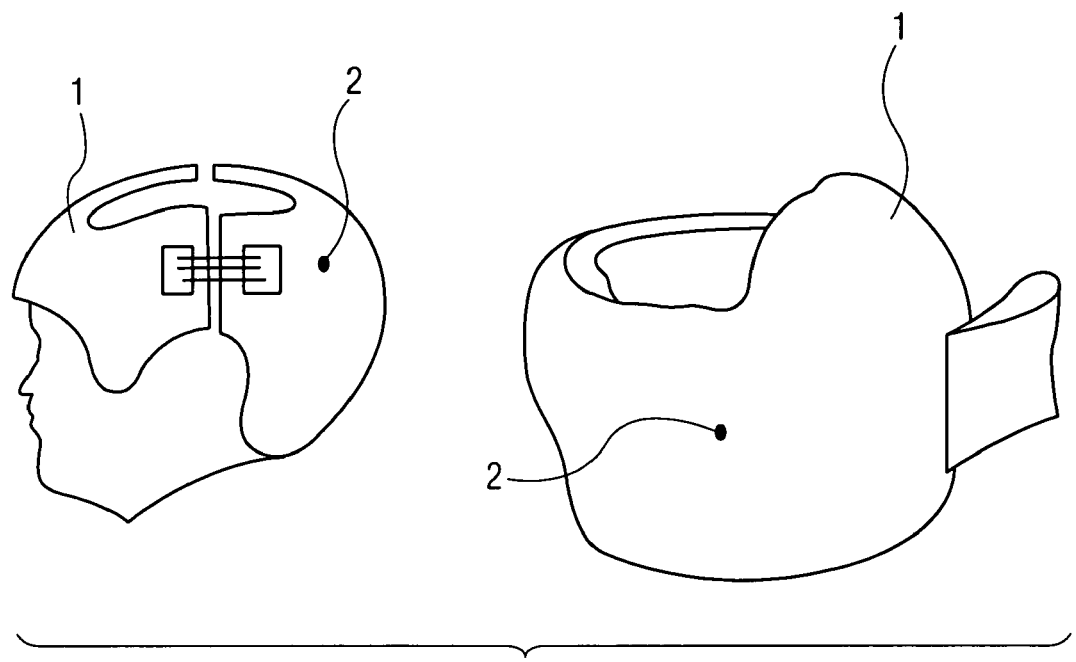
FIG. 2 shows a typical helmet design for use in dynamic orthotic cranioplasty helmet.

An analysis of typical helmets used in orthotic cranioplasty reveals that the main reason excessive sweating occurs is a lack of air vents. This lack of ventilation hinders heat dissipation and sweat evaporation. FIG. 2 shows one current helmet 1, in which it can be seen that the entire rear portion 2 of an infant's head is fully covered by the helmet 1 so that outside air cannot directly contact the head.

Figure 3:
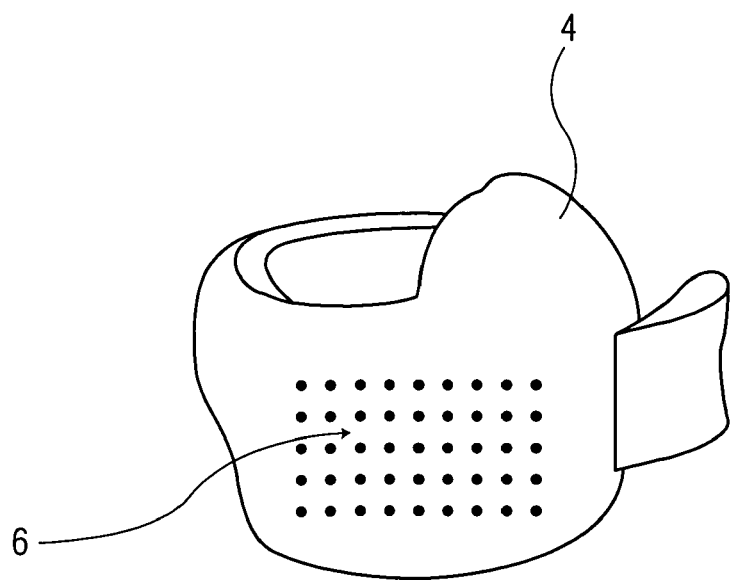
FIG. 3 shows the disclosed design helmet for temperature and sweat control, including a plurality of ventilation holes in the rear portion of the helmet.

FIG. 3 illustrates an exemplary helmet 4 incorporating an array of ventilation holes 6 according to the disclosed design. The design is simple in appearance and does not require additional expensive materials when compared to current helmets. Customization of the array of ventilation holes 6 for a particular patient may achieve optimal anti-sweat performance for that patient. Specifically, the ventilation design should be adaptive to the physiology of the individual infant's head, and may be guided by one or more of the following four factors: (1) the size of ventilation holes, (2) the distance between neighboring holes, (3) the pattern of the array, and (4) the distribution range of the array on the helmet. It will be appreciated that each factor may lead to a different anti-sweat effect. For example, larger holes may allow more air to pass through and thus achieve better cooling effect. However, overly-large holes may affect stability of the portion of the helmet in which the holes are placed, and thereby may adversely affect the treatment effect.

Figure 4A:
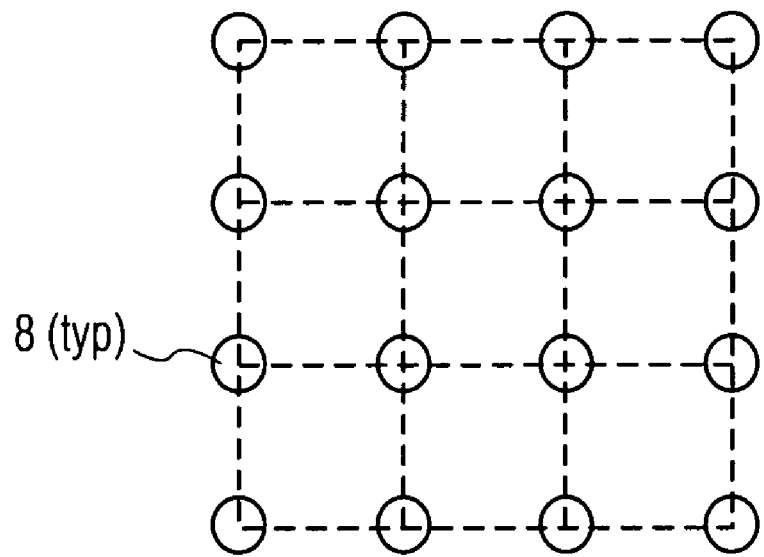
FIGS. 4a-4d are exemplary optional ventilation hole configurations for use with the helmet of FIG. 3.
Figure 4B:
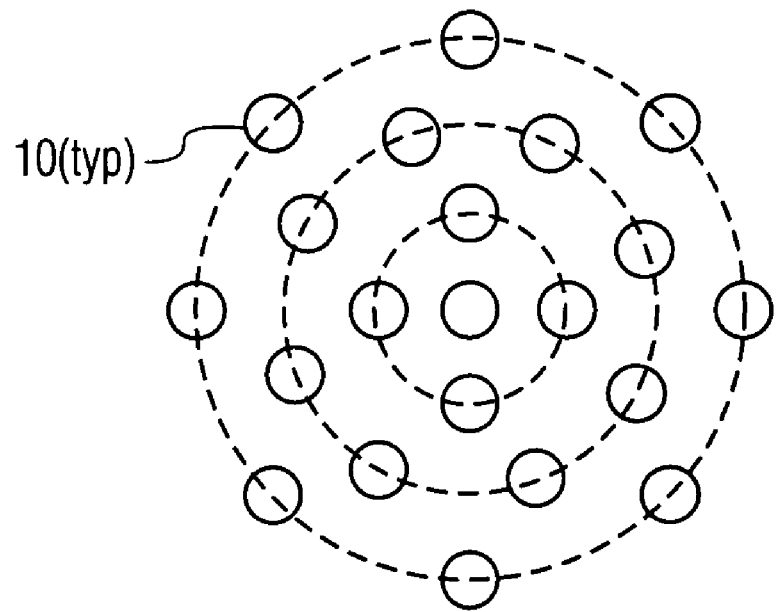
Figure 4C:
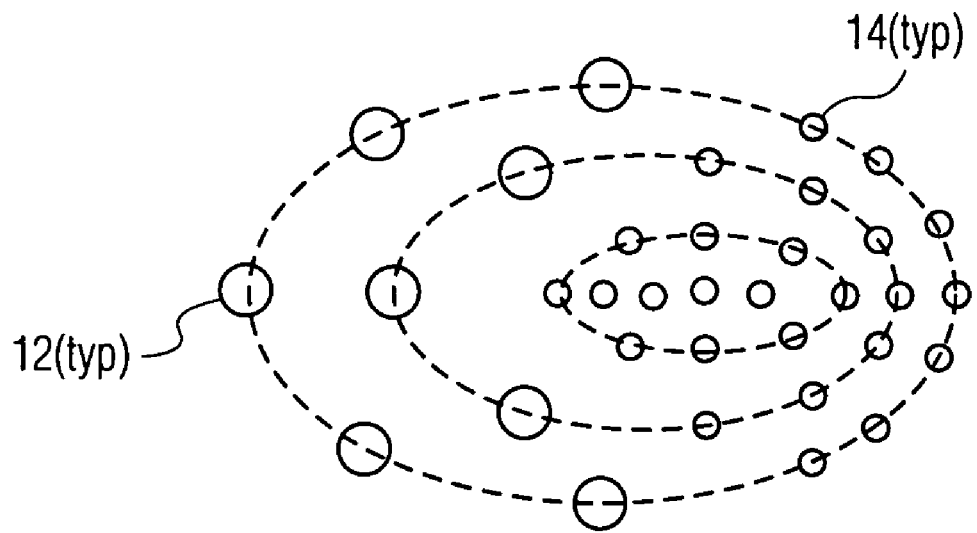
Figure 4D:
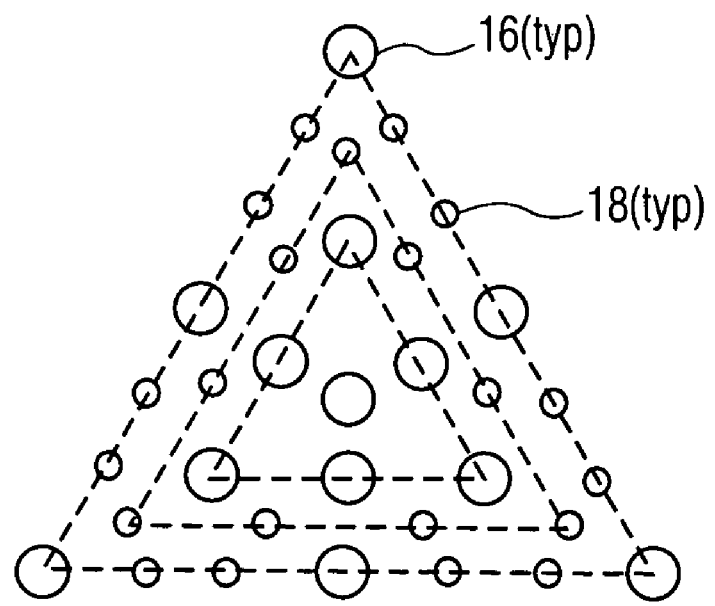

FIGS. 4a-c illustrate several exemplary ventilation hole array patterns that could be employed on one or more portions of a patient helmet. The pattern of FIG. 4a is a generally square arrangement of holes 8, the pattern of FIG. 4b is a generally circular arrangement of holes 10; the pattern of FIG. 4c is an asymmetric arrangement of holes 12, 14, while the pattern of FIG. 4d shows a triangular arrangement of holes 16, 18. As can be seen, the patterns of FIGS. 4a, 4b incorporate holes 8, 10 of a single size. By contrast, the patterns of FIGS. 4c, 4d incorporate multiple different-sized holes 12, 14; 16, 18. In addition, with the FIGS. 4c, 4d designs, the holes are not all spaced at equal intervals, but are placed at discrete and different intervals according to the needs of a particular patient. It will be appreciated that the illustrated patterns are merely several examples of possible array designs for ventilation holes, and that a wide variety of other arrangements are also contemplated.

The different array patterns and combinations of hole sizes may be employed to generate different anti-sweat effects. For instance, if a particular region of an infant patient's head is found to be overly susceptible to sweating, then an asymmetric shape such as that shown in FIG. 4c may be used so that a larger number of small holes are positioned to service that "high-sweat" region, while a smaller number of holes are positioned to service the regions of the head that are not so susceptible to sweating.

In order to achieve such a customized design, a variety of individual parameters relating to the patient may be obtained and analyzed in combination. A non-limited list of such parameters including the patient's age, head size, relative amount of sweat, average diameter and length of hair, range in which sweating is or is expected to occur, symmetry of the head, and the like. Table 1 below lists the input measurements of patient's information.

TABLE 1

| Patient's Information | |
|---|---|
| Patient's Information | Parameter |
| Helmet thickness (inch) | $l_t$ |
| Helmet diameter (inch) | $l_d$ |
| Patient's age (month) | $a_a$ |
| Amount of sweat (0~10) | $s_a$ |
| Diameter of patient's hair (0~5) | $h_d$ |
| Average length of patients hair (0~5) | $h_l$ |
| Sweat range (inch) | $R_s = (sx, sy)$ |

With respect to the "amount of sweat," "diameter of patient's hair," and "average length of patient's hair," a scale on the order of 0-10 may be used similar to pain indices used in hospitals. The practitioner will simply input a unit value corresponding to the patient's observed condition. Of course, it will be appreciated that a 0-10 scale is only one example, and others can also be used.

Table 2 below presents the main factors used in the automatic algorithm.

| Algorithm Factors | Factor |
|---|---|
| Hole size (inch) | H ($H_{min}$, $H_{max}$) |
| Distance between holes (inch) | D ($D_{min}$, $D_{max}$) |
| Distribution range (inch) | R |

The "distance between holes" provides minimum and maximum values between holes, while the "distribution range" provides a measure of the helmet area over which the user wishes to deploy the holes.

The formulas are as follows.

$H_{min}$ is a constant
$H_{max} = f_1(l_t) f_2(s_a)$
$H = f_3(l_t) f_4(s_a) f_5(h_d) f_6(h_l)$
$f_1, \ldots, f_6$ are different functions. For example, $$H_{max} = \frac{1}{k_{H1}} \exp\left\{\frac{l_t^2}{2\sigma_{H1}^2}\right\} \frac{1}{k_{H2}} \exp\left\{\frac{s_a^2}{2\sigma_{H2}^2}\right\}$$

$$H = \frac{1}{k_{H3}} \exp\left\{\frac{l_t^2}{2\sigma_{H3}^2}\right\} \frac{1}{k_{H4}} \exp\left\{\frac{s_a^2}{2\sigma_{H4}^2}\right\} \frac{1}{k_{H5}} \exp\left\{\frac{h_d^2}{2\sigma_{H5}^2}\right\} \frac{1}{k_{H6}} \exp\left\{\frac{h_l^2}{2\sigma_{H6}^2}\right\}$$

where $k_{H1}, \ldots, k_{H6}, \sigma_{H1}, \ldots, \sigma_{H6}$ are constants. For example, $\sigma_{H1}=1$, $\sigma_{H2}=2.7$, $\sigma_{H3}=1$, $\sigma_{H4}=2.7$, $\sigma_{H5}=2.1$, $\sigma_{H6}=2.1$, $k_{H1}=4.12$, $k_{H2}=3.86$, $k_{H3}=4.12$, $k_{H4}=3.86$, $k_{H5}=3.63$, $k_{H6}=3.63$.

$D_{min} = p_1(l_t) p_2(H_{max})$
$D_{max} = p_3(R)$
$D = p_1(l_t) p_2(H)$
$p_1, \ldots, p_3$ are different functions. For example, $$D_{min} = \frac{1}{k_{D1}} \exp\left\{\frac{l_t^2}{2\sigma_{D1}^2}\right\} \frac{1}{k_{D2}} \exp\left\{\frac{H_{max}^2}{2\sigma_{D2}^2}\right\}$$

$$D_{min} = \frac{1}{k_{D3}} \min(rx, ry)$$

where $k_{D1}, \ldots, k_{D3}, \sigma_{D1}, \sigma_{D2}$ are constants. For example, $k_{D1}=0.21$, $k_{D2}=2.51$, $k_{D3}=1$, $\sigma_{D1}=1$, $\sigma_{D2}=1$.

$R = g_1(R_s) g_2(l_d) g_3(a_a)$ $g_1, \ldots, g_3$ are different functions. For example, $$rx = \frac{1}{k_{rx}} \exp\left\{\frac{l_d^t a_a^2}{2\sigma_{rx}^2}\right\} sx$$

$$ry = \frac{1}{k_{ry}} \exp\left\{\frac{l_d^t a_a^2}{2\sigma_{ry}^2}\right\} sy$$

where $k_{rx}$, $r_{ry}$, $\sigma_{rx}$, $\sigma_{ry}$ are constants. For example $k_{rs}=14.18$, $k_{ry}=14.18$, $\sigma_{rx}=32$, $\sigma_{ry}=32$.

Figure 5:
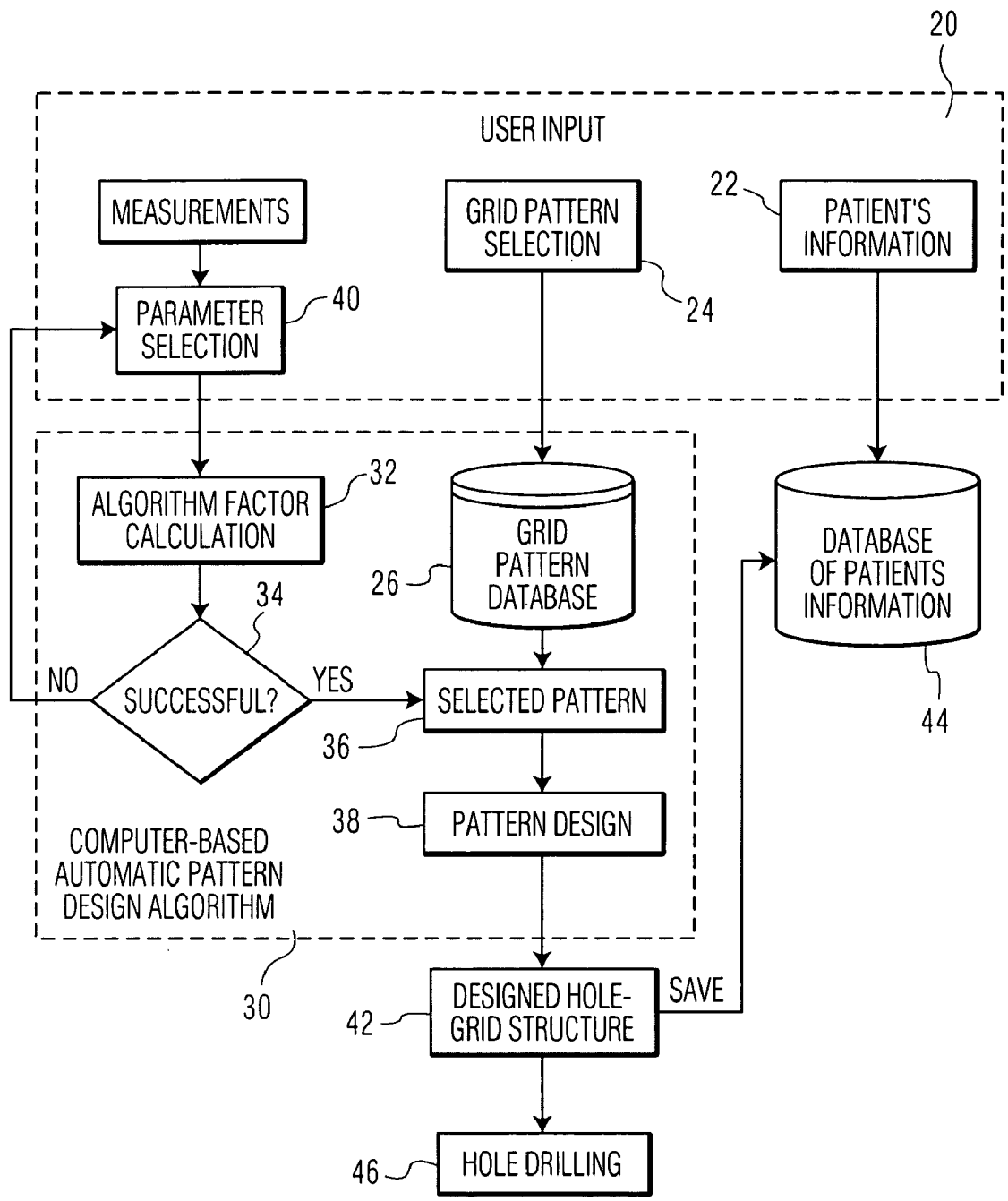
FIG. 5 is a flow chart showing an exemplary process for creating a patient-specific configuration of ventilation holes in a helmet.

FIG. 5 shows the pattern design workflow utilizing the above algorithm. As can be seen, in the user input module 20, the user inputs the patient's information at step 22 such as helmet diameter, thickness, amount of sweat, etc., and selects a desired grid pattern at step 24 from the grid pattern database 26. The user also registers the patient's other information (e.g., patient's name, gender, address and the like) into the computer database. The patient's parameters are fed into the algorithm at step 30, which automatically estimates the algorithm factors at step 32 for the patient in the manner described above. At step 34 algorithm determines whether the calculation is successful. For example, if $H_{min} \leq H \leq H_{max}$, $D_{min} \leq D \leq D_{max}$, are both satisfied, then the design is considered successful and at step 36 the selected factors will be applied to the selected pattern and at step 38 will further generate the pattern design. If $H_{min} \leq H \leq H_{max}$, $D_{min} \leq D \leq D_{max}$, are not both satisfied, the system will ask the user to adjust the input parameters at step 40. This process is continued until a successful calculation is achieved, indicating that the hole array design is appropriate for the patient based on the input factors provided by the user. At step 42, the "approved" hole-grid structure is saved in a database 44 for later application and is also used to implement the hole drilling at step 46. As will be described in greater detail later, this hole drilling can be manually applied to a pre-cast helmet, or it can be performed in an automated fashion by a computer controlled drilling machine. It will be appreciated that the holes could also be molded into the helmet as part of the overall helmet molding process. The helmet is then ready for use with the patient.

Figure 6:
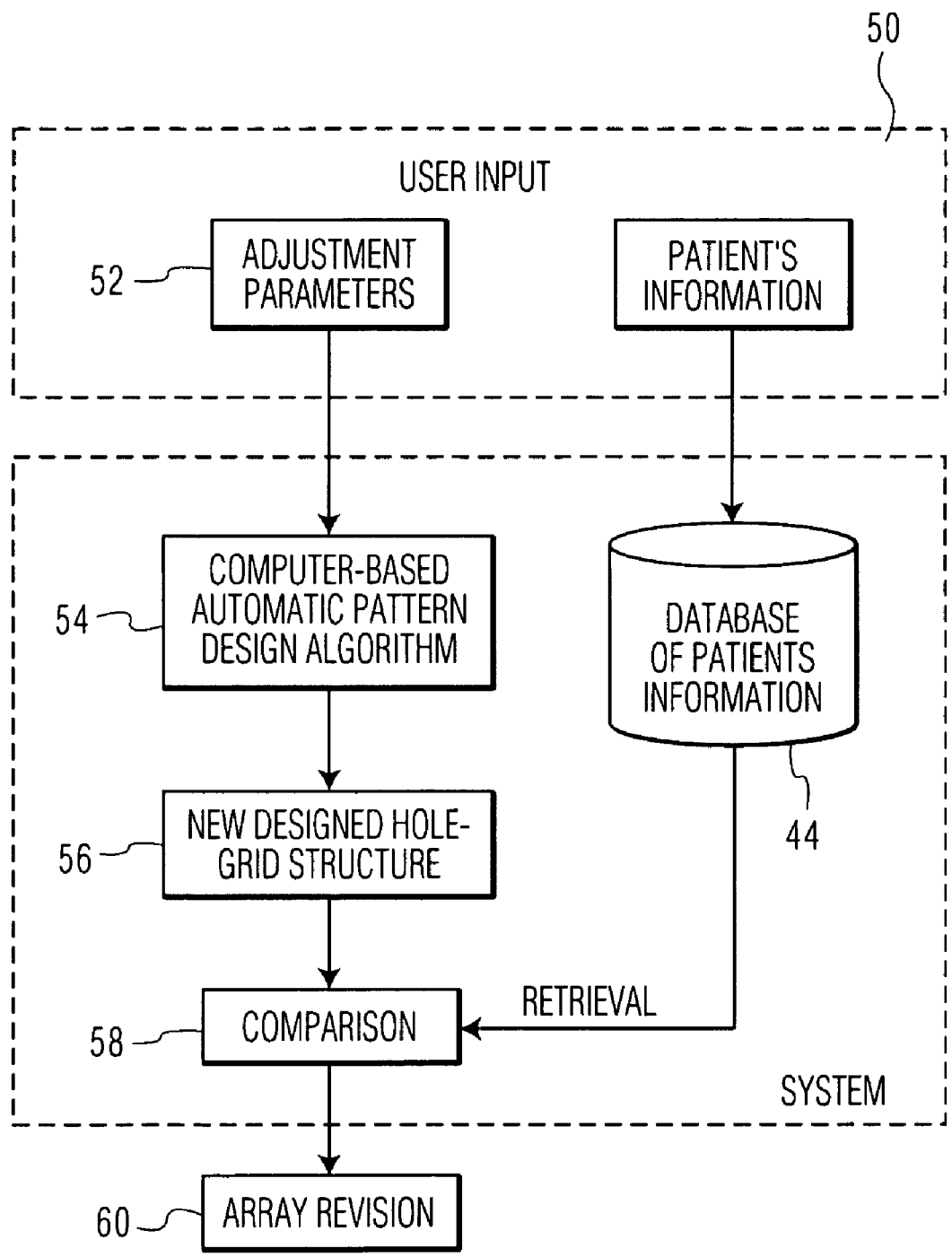
FIG. 6 is a flow chart showing an exemplary process for modifying the patient-specific configuration of ventilation holes as the patient's treatment progresses.

Typically the user will wear the helmet for a period of about three months for a patient less than one year hold. During this period the shape of the patient's head will change to approximate a desired shape based on the characteristics of the prosthesis. Thus, in many cases it may be desired to adjust the original ventilation hole array pattern to maintain optimal sweat and temperature control. This adjustment can be achieved in the manner shown in FIG. 6. At the user input module 50, the user may input the adjustment parameters into the system at step 52. These adjustment parameters may include a proposed revised hole size, revised distance between holes, and revised hole range. At step 54 the adjustment parameters are input to the algorithm described in relation to FIG. 5, and the system determines at step 56 whether the new designed ventilation array design is acceptable based on the new parameters. At step 58 the patient's previously used pattern can be retrieved from the patient information database 44 and compared with the new design. At step 60 the system can then drive a plastic injection molding machine or the hole drilling machine to change the hole structure on the helmet by either filling, drilling, or a combination of both. In one example, where a hole is no longer needed, the computer may drive a nozzle of the plastic injection molding machine 76 (see FIG. 7) to locate and fill the appropriate hole.

Figure 7:
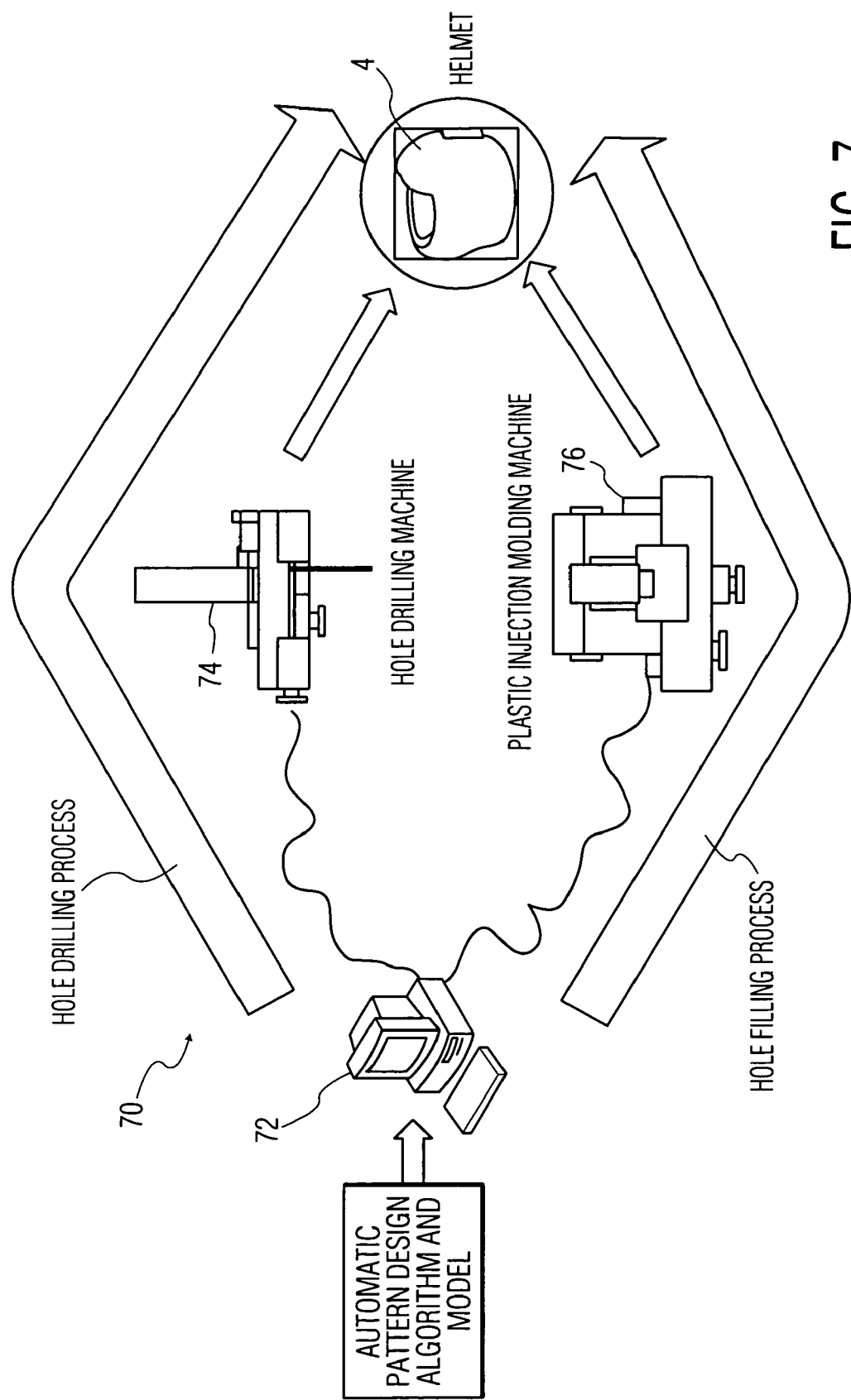
FIG. 7 is a schematic of a system used to generate a helmet incorporating a desired configuration of ventilation holes customized to a particular patient.

A system 70 for implementing the above method will now be described in relation to FIG. 7. The system 70 may be used to perform both the hole drilling process and the hole filling process. In the hole drilling process, the clinician firstly inputs parameters of the infant patient into a computer 72 that is running (or has stored in removable or permanent media) the algorithm described in relation to FIGS. 5 and 6. The computer 72, running the algorithm, determines whether the user proposed ventilation hole array meets the prescribed criteria (e.g., $H_{min} \leq H \leq H_{max}$, $D_{min} \leq D \leq D_{max}$). As previously noted, if the array does not meet the prescribed criteria, then a revised design is input and the algorithm determines whether the revised design is acceptable. This process continues until the criteria are met.

Once the optimal ventilation hole array design is achieved, the design is electronically transferred into a digital hole drilling machine 74 to drill the individual holes in the helmet according to the input design. The hole drilling machine 74 can be any of a variety of known designs, such as a laser-based machine or a mechanical drilling machine. The electronic transfer of the design could be achieved by hardwire or wireless connection between the computer 72 and the hole drilling machine. Alternatively, the electronic transfer could take place over a network (intranet, Internet, etc.), or the design could be downloaded to removable media and physically transferred to the hole drilling machine 74. It will also be appreciated that the drilling could be performed manually, by printing a template or otherwise transferring a physical representation of the hole array, applying the template/representation to a helmet "blank" and then manually drilling the holes at the desired locations.

As previously noted, the it may be desirable to modify the size or placement of the ventilation holes as the patient's treatment progresses. Thus, as described in relation to FIG. 6 a revised ventilation hole array design may be selected and "approved" using the aforementioned algorithm. Since the same helmet 4 will continue to be used, the revised ventilation hole array design may require the filling of certain holes and/or the drilling of new holes. Where holes are required to be filled, the design may be electronically transferred into a digital hole filling machine 76, such as a plastic injection molding machine. As with the hole drilling process, the electronic transfer of the design for the hole filling process may be achieved by hardwire or wireless connection between the computer 72 and the hole filling machine 76. Alternatively, the electronic transfer could take place over a network (intranet, Internet, etc.), or the design could be downloaded to removable media and physically transferred to the hole filling machine 76. It will also be appreciated that the filling could be performed manually using known filling techniques. Once the filling/drilling processes are completed, manual polishing of the helmet may be performed to result in a smooth surface.

This disclosed system and method presents an effective temperature and sweat control solution for dynamic orthotic cranioplasty in the treatment of positional plagiocephaly of infants' heads. The system and method can result in a helmet that decreases patient sweating by providing more open air to the occluded head range. Moreover, the system and method is adaptive to provide a customized design that addresses different infants' individual physical parameters. It will be appreciated that while the disclosed system and method may be appropriate for designing helmets used to treat positional plagiocephaly of infants, that the system and method may also be used in other applications where the reduction of sweating is desirable, such as any of a variety of sporting helmets, safety helmets, neck pads, chest protectors, and the like.

The system and technique described herein may be automated by, for example, tangibly embodying a program of instructions upon a computer readable storage media, capable of being read by machine capable of executing the instructions. A general purpose computer is one example of such a machine. Examples of appropriate storage media are well known in the art and would include such devices as a readable or writeable CD, flash memory chips (e.g., thumb drive), various magnetic storage media, and the like.

The features of the system and technique have been disclosed, and further variations will be apparent to persons skilled in the art. All such variations are considered to be within the scope of the appended claims. Reference should be made to the appended claims, rather than the foregoing specification, as indicating the true scope of the subject system and technique.

What is claimed is:

1. A method for providing a customized orthopedic helmet, comprising:
   drilling an array of ventilation holes having a determined placement and size in an orthopedic helmet and customized to a particular patient; and
   determining at least one of: (a) said placement of the array of ventilation holes, and (b) said size of at least one of the ventilation holes, in response to a parameter comprising at least one of: helmet thickness, helmet diameter, patient age, degree of patient sweating, diameter of patient's hair, average length of patient's hair, and sweat range.

2. The method of claim 1, wherein
   the step of drilling an array of ventilation holes further comprises drilling the array of ventilation holes in a particular portion of the orthopedic helmet and
   the determining step comprises determining said placement of the array of ventilation holes and said size of at least one of the ventilation holes, in response to said parameter.

3. The method of claim 2, wherein
   the drilling step is performed by a computer controlled drilling machine.

4. The method of claim 1, wherein
   a configuration of the array of ventilation holes is selected from the group consisting of rectangular, triangular and circular.

5. The method of claim 1, wherein
   a configuration of the array of ventilation holes comprises at least two ventilation holes of different size.

6. The method of claim 1, further comprising
   the step of revising the placement of the array of ventilation holes based on the change in shape of the patient's head during treatment, the step of revising comprising at least one of: (a) filling an existing ventilation hole, (b) drilling a new ventilation hole, and (c) changing the size of an existing ventilation hole.

7. The method of claim 6, wherein
   the revising step comprises filling at least one of the array of ventilation holes with an automated injection molding device.

8. A system for providing a customized orthopedic helmet, comprising:
   means for drilling an array of ventilation holes having a determined placement and size in an orthopedic helmet and customized to a particular patient; and
   means for determining at least one of: (a) said placement of the array of ventilation holes, and (b) said size of at least one of the ventilation holes, in response to a parameter selected from the list consisting of: helmet thickness, helmet diameter, patient age, degree of patient sweating, diameter of patient's hair, average length of patient's hair, and sweat range.

9. The system of claim 8, wherein
   the means for drilling an array of ventilation holes having a determined placement and size in an orthopedic helmet further comprises means for drilling the array of ventilation holes in a particular portion of the orthopedic helmet and comprises determining both said placement of the array of ventilation holes and said size of at least one of the ventilation holes, in response to said parameter.

10. The system of claim 9, wherein
    the means for drilling comprises a computer controlled drilling machine.

11. The system of claim 8, wherein
    a configuration of the array of ventilation holes is selected from the group consisting of rectangular, triangular and circular.

12. The system of claim 8, wherein
    a configuration of the array of ventilation holes comprises at least two ventilation holes of different size.

13. The system of claim 8, further comprising
    means for revising the placement of the array of ventilation holes based on the change in shape of the patient's head during treatment, the means for revising comprising at least one of: (a) means for filling an existing ventilation hole, (b) means for drilling a new ventilation hole, and (c) means for changing the size of an existing ventilation hole.

14. The system of claim 13, wherein
    the means for revising comprises an automated injection molding device.

15. A machine readable storage device tangibly embodying a series of instructions executable by a machine to perform a series of steps, the steps comprising:
    drilling an array of ventilation holes having a determined placement and size in an orthopedic helmet and customized to a particular patient; and
    determining at least one of (a) said placement of the array of ventilation holes, and (b) said size of at least one of the ventilation holes, in response to a parameter comprising at least one of: helmet thickness, helmet diameter, patient age, degree of patient sweating, diameter of patient's hair, average length of patient's hair, and sweat range.

16. The machine readable storage device of claim 15, wherein
    the step of drilling an array of ventilation holes further comprises drilling the array of ventilation holes in a particular portion of the orthopedic helmet and
    the determining step comprises determining said placement of the array of ventilation holes and said size of at least one of the ventilation holes, in response to said parameter.

17. The machine readable storage device of claim 16, wherein
    the drilling step is performed by a computer controlled drilling machine.

18. The machine readable storage device of claim 15, wherein a configuration of the array of ventilation holes is selected from the group consisting of rectangular, triangular and circular.

19. The machine readable storage device of claim 15, wherein a configuration of the array of ventilation holes comprises at least two ventilation holes of different size.

20. The machine readable storage device of claim 15, further comprising the step of revising the placement of the array of ventilation holes based on the change in shape of the patient's head during treatment, the step of revising comprising at least one of: (a) filling an existing ventilation hole, (b) drilling a new ventilation hole, and (c) changing the size of an existing ventilation hole.

* * * * *